United States Patent
Baker et al.

(10) Patent No.: US 6,427,084 B2
(45) Date of Patent: *Jul. 30, 2002

(54) MULTI-SITE HYBRID HARDWARE-BASED CARDIAC PACEMAKER

(75) Inventors: Kenneth L. Baker; Doug M. Birkholz, both of Shoreview; David L. Perschbacher, Coon Rapids; Andrew P. Kramer, Stillwater; Gary T. Seim, Minneapolis, all of MN (US)

(73) Assignee: Cardiac Pacemakers, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/514,813

(22) Filed: Feb. 28, 2000

Related U.S. Application Data

(63) Continuation-in-part of application No. 09/378,793, filed on Aug. 23, 1999.

(51) Int. Cl.[7] .............................................. A61N 1/362
(52) U.S. Cl. ......................................................... 607/9
(58) Field of Search ................................ 607/9, 10, 11, 607/12, 13, 14, 15, 16, 27, 28, 29, 30

(56) References Cited

U.S. PATENT DOCUMENTS

| | | |
|---|---|---|
| 4,378,020 A | 3/1983 | Nappholz et al. |
| 4,407,288 A | 10/1983 | Langer et al. ......... 128/419 PG |
| 4,503,857 A | 3/1985 | Boute et al. .......... 128/419 PG |
| 4,554,920 A | 11/1985 | Baker, Jr. et al. ..... 128/419 PG |
| 4,577,633 A | 3/1986 | Berkovits et al. |
| 4,779,617 A | 10/1988 | Whigham |
| 4,928,688 A | 5/1990 | Mower ................. 128/419 PG |
| 5,022,395 A | 6/1991 | Russie .................. 128/419 PG |
| 5,081,987 A | 1/1992 | Nigam ................. 120/419 PG |
| 5,085,215 A | 2/1992 | Nappholz et al. |
| 5,103,820 A | 4/1992 | Markowitz |
| 5,292,340 A | 3/1994 | Crosby et al. ................ 607/17 |
| 5,312,450 A | 5/1994 | Markowitz ................... 607/14 |
| 5,360,437 A | 11/1994 | Thompson .................... 607/30 |
| 5,643,326 A | 7/1997 | Weiner et al. ................ 607/14 |
| 5,776,168 A | 7/1998 | Gunderson ................... 607/27 |
| 5,792,203 A | 8/1998 | Schroeppel .................. 607/30 |
| 6,026,324 A | 2/2000 | Carlson ........................ 607/27 |
| 6,129,745 A | 10/2000 | Sun et al. ..................... 607/27 |

OTHER PUBLICATIONS

Bakker, P.F., et al., "Beneficial Effects of Biventricular Pacing in Congestive Heart Failure", *PACE*, 17 (4), Part II, NASPE Abstract No. 318, 1 p., (Apr. 1994).

Gaggini, G., et al., "Mixed Microprocessor–Random Logic Approach for Innovative Pacing Systems", *Pacing and Clinical Electrophysiology*, 15 (11), pp. 1858–1861, (Nov. 1992).

Stotts, L.J., et al., "An 8–bit Microcomputer with Analog Subsystems for Implantable Biomedical Application", *IEEE Journal of Solid–State Circuits*, 24 (2), pp. 292–300, (Apr. 1989).

*Primary Examiner*—Scott M. Getzow
(74) *Attorney, Agent, or Firm*—Schwegman, Lundberg, Woessner & Kluth P.A.

(57) ABSTRACT

A hybrid cardiac pacemaker in which the operation of the device is controlled by hardware-based controller as supervised by a microprocessor-based controller. The hardware-based controller comprises a plurality of timers that expire when they reach timer limit values stored in registers updatable by the microprocessor, and a combinational logic array for causing the device to generate pace outputs in accordance with timer expirations and sense signals. The combinational logic array may operate the pacemaker in a number of programmed modes in accordance with a mode value stored in a mode control register by the microprocessor.

24 Claims, 4 Drawing Sheets

MULTI-SITE HYBRID HARDWARE-BASED CARDIAC PACEMAKER

CROSS REFERENCE TO RELATED APPLICATIONS

This application is a continuation-in-part of U.S. patent application Ser. No. 09/378,793, filed on Aug. 23, 1999, the specification of which is incorporated herein by reference.

FIELD OF THE INVENTION

This invention pertains generally to the field of cardiac pacemakers and implantable cardioverter/defibrillators incorporating a pacing function. In particular, the invention relates to the hardware and software used to control the operation of such devices.

BACKGROUND

Most cardiac pacemakers today (including implantable cardioverter/defibrillators with pacing capability) are microprocessor-based systems in which software run by the microprocessor commands the generation of pacing outputs, with various timers being used to alert the microprocessor as to when to pace. Such microprocessor-based systems exhibit great flexibility, as compared with a pacemaker implemented with dedicated hardware, since the operation of the device can be changed simply by reprogramming the microprocessor. Controlling the operation of a pacemaker totally with a microprocessor-based system, however, also has some disadvantages. If the microprocessor continually executes instructions during the cardiac cycle in order to process and respond to timing and sensing events, a large amount of battery power is consumed. Also, making pacing decisions with software inevitably introduces some variability into the timing of the paces, commonly referred to as "pacing jitter."

SUMMARY OF THE INVENTION

The present invention is embodied by a pacemaker that employs a hybrid microprocessor-based and hardware-based system to control its operation. In an exemplary embodiment, the pacemaker may be configured to pace in any of a number of different pacing modes, including biventricular pacing modes. In accordance with the invention, a plurality of hardware timers define particular timing intervals to which the pacemaker responds. For each timer, a compare register writable by a microprocessor-based controller is used to store a specified limit value for the timer, and a comparator generates a timer expiration signal for each timer when the output of the timer equals the limit value. The microprocessor can update the limit values of each compare register between cardiac cycles as defined by the expiration of a particular timer. Sensing channels may be provided for an atrium and/or ventricle, which sensing channels include a sense amplifier for amplifying a voltage from an electrode in electrical contact with a heart chamber and thereby detecting depolarizations occurring in the heart chamber. Ventricular and/or atrial stimulus generators are provided for generating paces by outputting pacing voltage pulses to electrodes in contact with the heart chamber to be paced. A combinational logic array interprets detected depolarization signals in order to generate sensing signals and triggers the stimulus generator in response to the expiration of particular timers and the generation of particular sense signals in accordance with a programmed pacing mode. A mode control register writable by the microprocessor contains a mode value stored by the microprocessor-based controller such that the combinational logic array enables or disables certain timers so as to cause the pacemaker to operate in a particular pacing mode in accordance with the mode value.

DETAILED DESCRIPTION OF THE INVENTION

Figure 1:
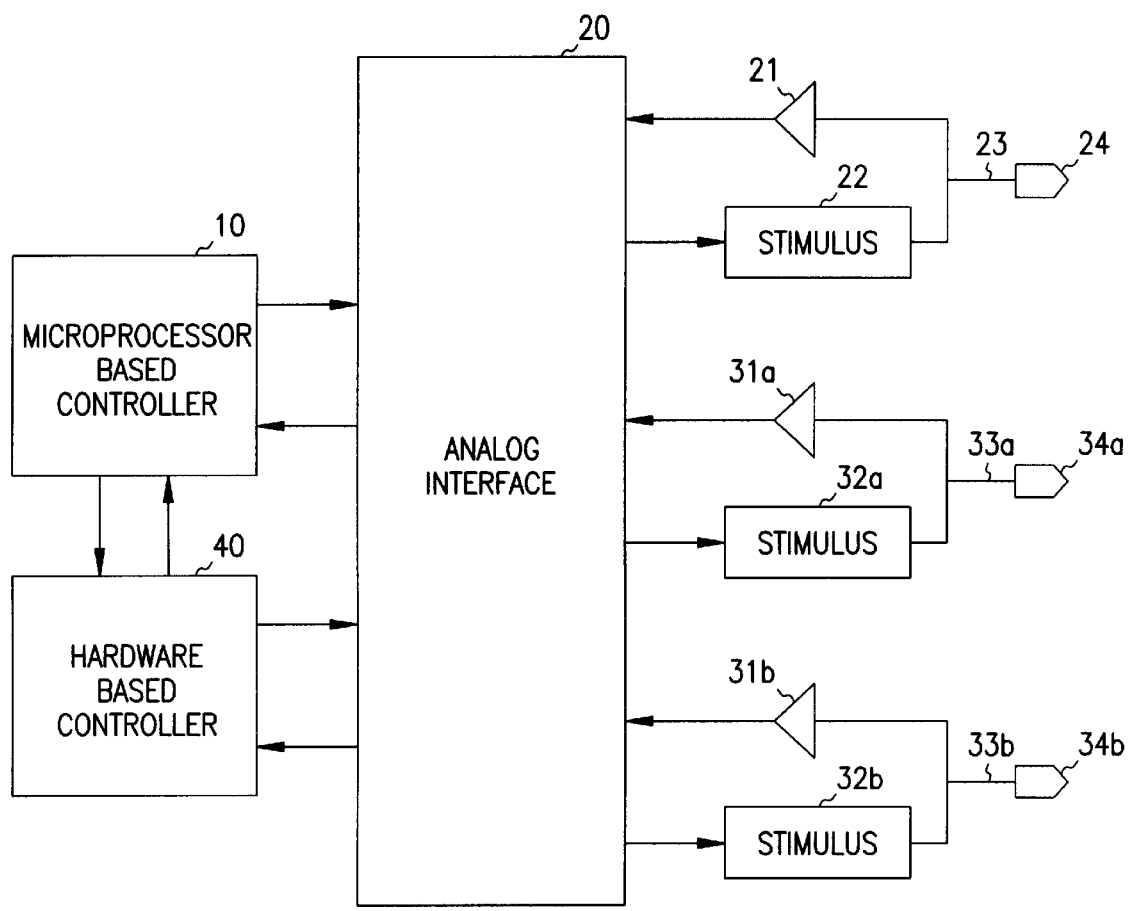
FIG. 1 is a system diagram of a pacemaker in accordance with the invention.

As aforesaid, a pacemaker in accordance with the present invention uses a hybrid microprocessor and hardware based controller for outputting pacing pulses in response to timer outputs and sensed cardiac events. The hardware-based controller uses dedicated timers for specific timing intervals, and a hardware implemented combinational logic array makes decisions as to when to take specific actions. Inputs to the logic array include timer status and pacing mode settings. The actions taken by the logic array include starting timers, stopping timers, pacing, and waking up the microprocessor software when needed. Events and actions are time stamped and buffered for the microprocessor software to save. The microprocessor software writes to registers in the hardware controller in order to define pacing modes and timer intervals. The software normally wakes up to set or adjust timer durations or define a pacing mode only at the end of the cardiac cycle. Since the hardware controller issues pacing commands and resets timers automatically, the amount of time in which the software needs to be active is thereby minimized. The hardware controller also works on a fixed clock cycle so that it makes and implements decisions on a regular basis, thus eliminating pacing jitter.

As noted, the hardware register has a control register to which the microprocessor writes in order to define a pacing mode. The modes employed for bradycardia pacing are usually described by a three-letter code developed by the Inter-Society Commission for Heart Disease where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used which implies a tracking mode), and O (for no response). Additional sensing of physiological data allows some pacemakers to change the rate at which they pace the heart in accordance with some parameter correlated to metabolic demand. Such pacemakers are called rate-adaptive and designated by a fourth letter added to the three-letter code, R. A pacemaker may be implemented in accordance with the present invention which is capable of pacing in any of these modes.

Pacemakers have been constructed for delivering pacing pulses to multiple ventricular or atrial sites, including so-called biventricular pacemakers where pacing pulses are delivered to both ventricles by separate electrodes during a cardiac cycle. (See, e.g., U.S. Pat. Nos. 5,792,203 and 4,928,688, referred to herein as the '203 and '688 patents, which are hereby incorporated by reference.) One type of multi-site pacing involves fixing two or more pacing electrodes to separate sites of the same heart chamber, either an atrium or a ventricle. For example, one electrode may be fixed to the apical region of either the right or left ventricle with the other electrode fixed to a basal region of the same ventricle. In the case of the left ventricle, this may be most easily accomplished by using a coronary sinus lead (See U.S. Pat. No. 5,935,160, hereby incorporated by reference) with distal and proximal electrodes. The ventricle can be paced in accordance with a programmed pacing mode with the electrodes being energized simultaneously during each pacing output in order to achieve near simultaneous activation of the ventricle. Alternatively, the pacing stimuli can be delivered to the ventricular electrodes sequentially with a specified time delay in order to take into account differing conduction times within the ventricle.

In the description of a specific embodiment that follows, the pacemaker is a biventricular dual-chamber pacemaker (where a single-chamber mode paces either the atria or ventricles, and a dual-chamber mode paces both the atria and ventricles). The pacemaker to be described has two ventricular sensing/pacing channels and a single atrial sensing/ pacing channel, and may be operated in any of a number of conventional single or dual-chamber pacing modes as described above, or a biventricular pacing mode where each ventricle may be paced during a cardiac cycle via a separate pacing channel. The pacemaker can be programmed to pace the atrium only, the right or left ventricle only, or both ventricles with a specified time delay.

FIG. 1 shows a system diagram of a hybrid microprocessor and hardware-based biventricular dual-chamber pacemaker in accordance with the invention. A microprocessor-based controller 10 includes a microprocessor and memory (typically a ROM for program storage and a RAM for data storage) and communicates with sensing/pacing channels through the analog interface 20. Sensing and pacing channels are provided for both the right and left ventricles that comprise, respectively, electrodes 34a and 34b, leads 33a and 33b, sense amplifiers 31a and 31b, and stimulus generators 32a and 32b. A atrial sensing/pacing channel similarly comprises electrode 24, lead 23, sense amplifier 21, and a stimulus generator 22. The analog interface 20 includes analog-to-digital converters for digitizing sensing signal inputs from the sense amplifiers and registers which can be written to by the hardware controller 40 in order to output pacing pulses. The hardware controller 40 receives detect signals indicating depolarizations in the atrium or ventricle from the analog interface 20. The analog interface 20 has blanking circuitry to prevent the generation of detect signals during the output of pacing pulses. The hardware controller 40 generates sensing signals from the detect signals, using the state of particular timers in some cases to interpret the detect signals. The controller 40 also generates pacing commands to the analog interface 20 in response to sensed events and particular timer states in accordance with a programmed pacing mode. Timers are implemented in the controller with counters that are compared to limit values stored in compare registers. Particular timers, as determined by the specified pacing mode, are started and stopped in response to particular sensed events by logic circuitry in the controller. The hardware controller 40 also has registers to which the microprocessor controller 10 can write in order to command a particular pacing mode and define timer expiration values.

Figure 2:
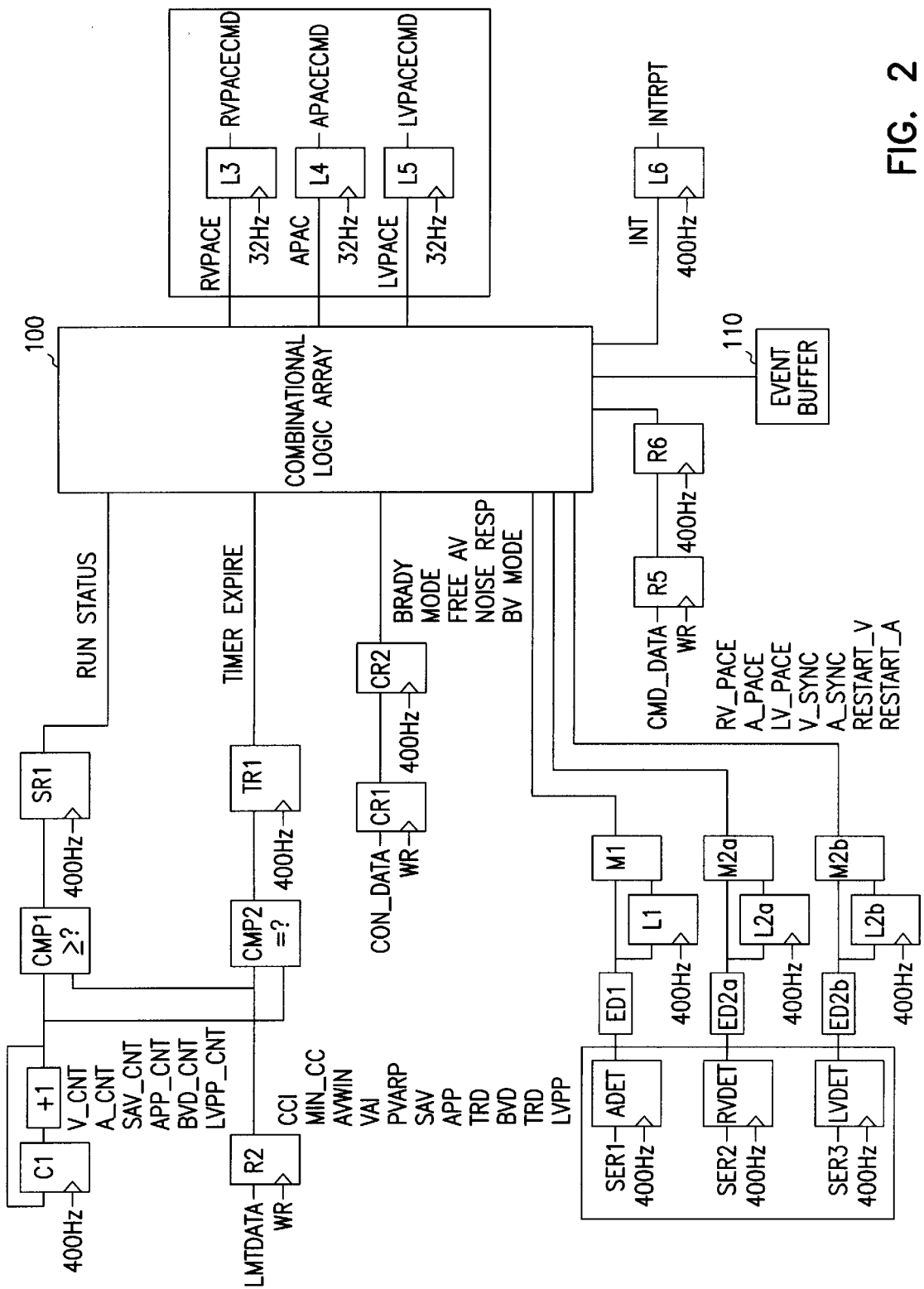
FIG. 2 is a block diagram showing the components of the hardware-based controller.

FIG. 2 is a block diagram of the hardware controller 40. Microprocessor 10 clocks a control data signal CON_DATA into the control register CR1 with write strobe signal WR in order to define a bradycardia pacing mode, define the response of the device when a specified noise level is present, define whether the atrial timers operate independently from the ventricular timers, and specify a biventricular pacing mode. The value in the control register is clocked into register CR2 and then input into the combinational logic array 100. (The clock signal frequencies shown in the figure are exemplary only.) The embodiment described here thus allows the pacemaker to pace in a number of pacing modes as controlled by the logic array 100.

A bank of counters C1 provides a ventricular counter V_CNT, an atrial counter A_CNT, a sensed AV interval counter SAV_CNT, an atrial protective period counter APP_CNT, a biventricular delay counter BVD_CNT, and a left ventricular protective period counter LVPP_CNT. The outputs of these counters are compared with limit values LMTDATA stored in the bank of compare registers R2 by the microprocessor 10 in order to define a timer for each of the limit values. The cardiac cycle interval CCI, minimum cardiac cycle interval MINCC, and minimum AV window AVWIN limit values are compared with the ventricular counter. The ventriculo-atrial interval VAI and the post-ventricular refractory period PVARP limit values are compared with the atrial counter. Unless the FREEAV bit in CR1 is set (designated FREEAV_T), the atrial and ventricular counters are both started/reset synchronously by either a ventricular pace or a right ventricular sense. If the FREEAV bit is not set (designated FREEAV_F), the atrial and ventricular counters are operated independently such that the combinational logic array resets the VAI and PVARP timers after an atrial pace, or an atrial sense if the pacemaker is operating in an atrial inhibited pacing mode, instead of after a ventricular sense or pace.

The sensed atrio-ventricular interval SAV, atrial protective period APP, and left ventricular protective period limit values are compared with the SAV_CNT, APP_CNT, and LVPP_CNT counters, respectively. The biventricular delay interval BVD and trigger delay TRD limit values are compared with the BVD_CNT counter. Comparator CMP1 compares the counter values with the limit values and asserts a logical one if the counter exceeds the limit value to indicate an expired status of the timer defined by the limit value. The output of CMP1 is clocked into register SR1 for indicating the run status of the timers to the logic array 100. Comparator CMP2 compares the limit values to the outputs of the corresponding timers, and asserts a logical one when the limit value equals the counter output. The output of comparator CMP2 is clocked into register TR1 to indicate expiration of the timer defined by the corresponding limit value to the logic array 100.

Serial signals SER1 through SER3 indicating the detection of atrial, right ventricular, and left ventricular depolarizations input from the analog interface 40 are clocked into latches ADET, RVDET, and LVDET respectively. The outputs of ADET and the ventricular latches are input to edge detectors ED1 and ED2a–b, respectively, and then input to the logic array 100. Latches L1 and L2a–b, and multiplexers M1 and M2a–b, provide a single clock cycle delay for the atrial and ventricular depolarization detect signals when the device is operating in either an atrial or ventricular triggered mode (indicated by the assertion of ATRIGMD and VTRIGMD, respectively, to the multiplexers) so that a pace command will not be inhibited by a sense signal. The microprocessor 10 issues commands to the logic array 100 by writing command data COM_DATA to register R5, which data is clocked into register R6 for inputting to logic array 100. The microprocessor 10 may issue pacing commands (RV_PACE, A_PACE, or LV_PACE), timer restart commands (RESTART_V or RESTART_A), and synchronization commands (V_AYNC or A_SYNC) that command the timers to be reset in accordance with the programmed mode as if a pace were output. The logic array 100 issues right ventricular, atrial, and left ventricular pace commands by asserting the signals RVPACE, APACE, and LVPACE which are clocked into latches L3, L4, and L5, respectively, for inputting to the analog interface 40 as commands RVPACECMD, APACECMD, and LVPACECMD, respectively. The logic array 100 may also generate a microprocessor interrupt by asserting the signal INT which is clocked into latch L6, the output of which is tied to an interrupt line of the microprocessor 10 as the signal INTRPT. The combinational logic array may generate interrupts to the microprocessor-based controller upon expiration of a timer, generation of a sense signal, or generation of a pacing output.

The combinational logic array 100 triggers the ventricular stimulus generators in accordance with the state of the CCI timer as well as the BVD and/or TRD timers in the case of biventricular delay and biventricular triggered pacing modes, respectively. Both the atrial and ventricular pacing modes are specified by bits of the control register CR1. Whether the atria or ventricle are paced (or not) are specified by bits designated as APACEMODE_T (or APACEMODE_Y) and VPACEMODE_T (or VPACEMODE_F), respectively. Whether atrial pacing is inhibited or triggered by an atrial sense is determined by a bit designated as ARESPMODE_IH or ARESPMODE_TG, respectively. Similarly, whether ventricular pacing is inhibited or triggered by a right ventricular sense is determined by a bit designated as VRESPMODE_IH or VRESPMODE_TG, respectively. The bits of CR1 that specify which ventricle or ventricles are to be paced are designated as CH_R for right ventricle only, CH_L for left ventricle only, CH_RL for a biventricular pacing mode in which a right ventricle pace is followed by a left ventricle pace, and CH_LR for a biventricular pacing mode in which the a left ventricle pace is followed by a right ventricle pace.

The minimum rate at which a ventricular pacemaker allows the heart to beat is determined by the ventricular escape interval and is sometimes referred to as the lower rate limit (LRL). In this embodiment, if ventricular pacing is enabled, the ventricular escape interval is the limit value of the cardiac cycle timer CCI. The CCI timer is thus started/reset by a right ventricular sense or pace, and its expiration generates a ventricular pace. If the ventricle(s) is paced in an atrial tracking mode (designated by a bit in CR1 as ARESPMODE_TK), expiration of the sensed AV interval timer SAV also results in the generation of a ventricular pace. The timer SAV is started by an atrial sense or pace if it is not already running, stopped by a ventricular sense or pace, and thus defines an escape interval in which a ventricular pace will be delivered if no ventricular sense occurs subsequent to an atrial sense or pace. The maximum rate at which ventricular pacing will track the atria is determined by the limit value of the minimum cardiac cycle timer MINCC. The logic array 100, when the pacemaker is programmed to operate in an atrial tracking mode, prevents delivering a ventricular pace upon expiration of the SAV timer if the MINCC timer is unexpired.

Biventricular pacing may be delivered by the device in either a triggered or demand mode as specified by a bit in CR1 designated VRESPMODE_TG or VRESPMODE_IH, respectively. In the former, a right ventricular sense triggers pacing of one ventricle (the primary pace) followed by pacing of the other ventricle (the secondary pace), with the delay specified by the limit value of the triggered delay timer TRD. In the latter, the pacing of one ventricle is controlled by the CCI and/or SAV timers with a pace delivered to the other ventricle within a time specified by the limit value of the biventricular delay timer BVD.

If atrial pacing is enabled in a demand mode, the atrial escape interval is specified by the limit value of the ventriculo-atrial interval timer VAI. The combinational logic array 100 triggers the atrial stimulus generator 32 upon expiration of the VAI timer, stops the VAI upon an atrial sense or pace, and resets the VAI timer upon a right ventricular sense or a ventricular pace. The PVARP timer is started upon a right ventricular sense or pace (if FREEAV_F is asserted) and prevents generation of an atrial sense signal if the PVARP timer is unexpired. The atrial protective period (APP) timer is started upon detection of an atrial depolarization and prevents generation of an atrial sense or an atrial pace if the APP timer is unexpired. The minimum AV window AVWIN timer is started after a ventricular pace or right ventricular sense and prevents generation of an atrial pace after expiration of the APP timer if the AVWIN timer is expired.

A noise inhibit (NSI) control bit is also be included such that when the bit is set, the combinational logic array 100 inhibits generation of pacing pulses if a noise level as sensed by the sensing channels exceeds a specified level. An event buffer register 110 readable by the microprocessor-based controller is also included in the hardware-based controller, where the combinational logic array stores event values in the event buffer register corresponding to the occurrence of specified events, including generation of sense signals, generation of pacing outputs, and expiration of timers. The event buffer may also contain interval data and time stamps for stored event values.

Figure 3A:
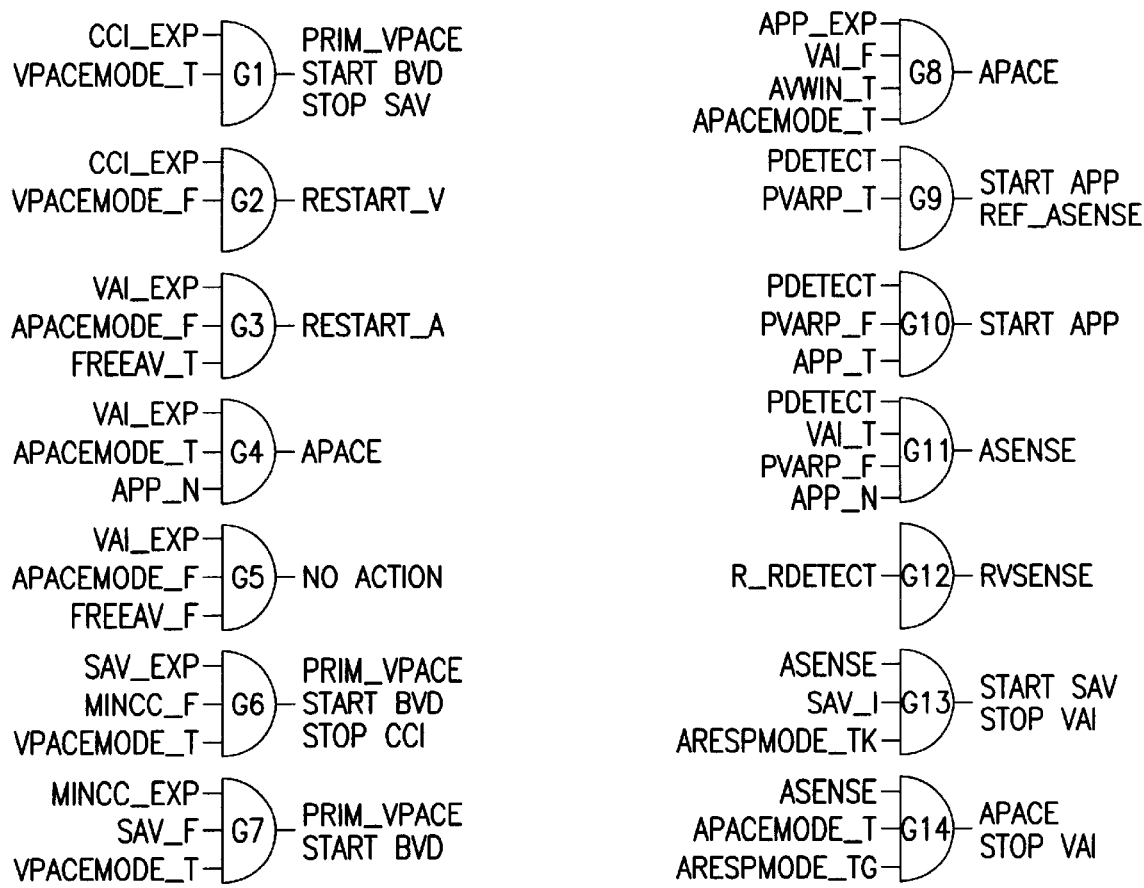
FIGS. 3A and 3B is a functional logic diagram of the combinational logic array.
Figure 3B:
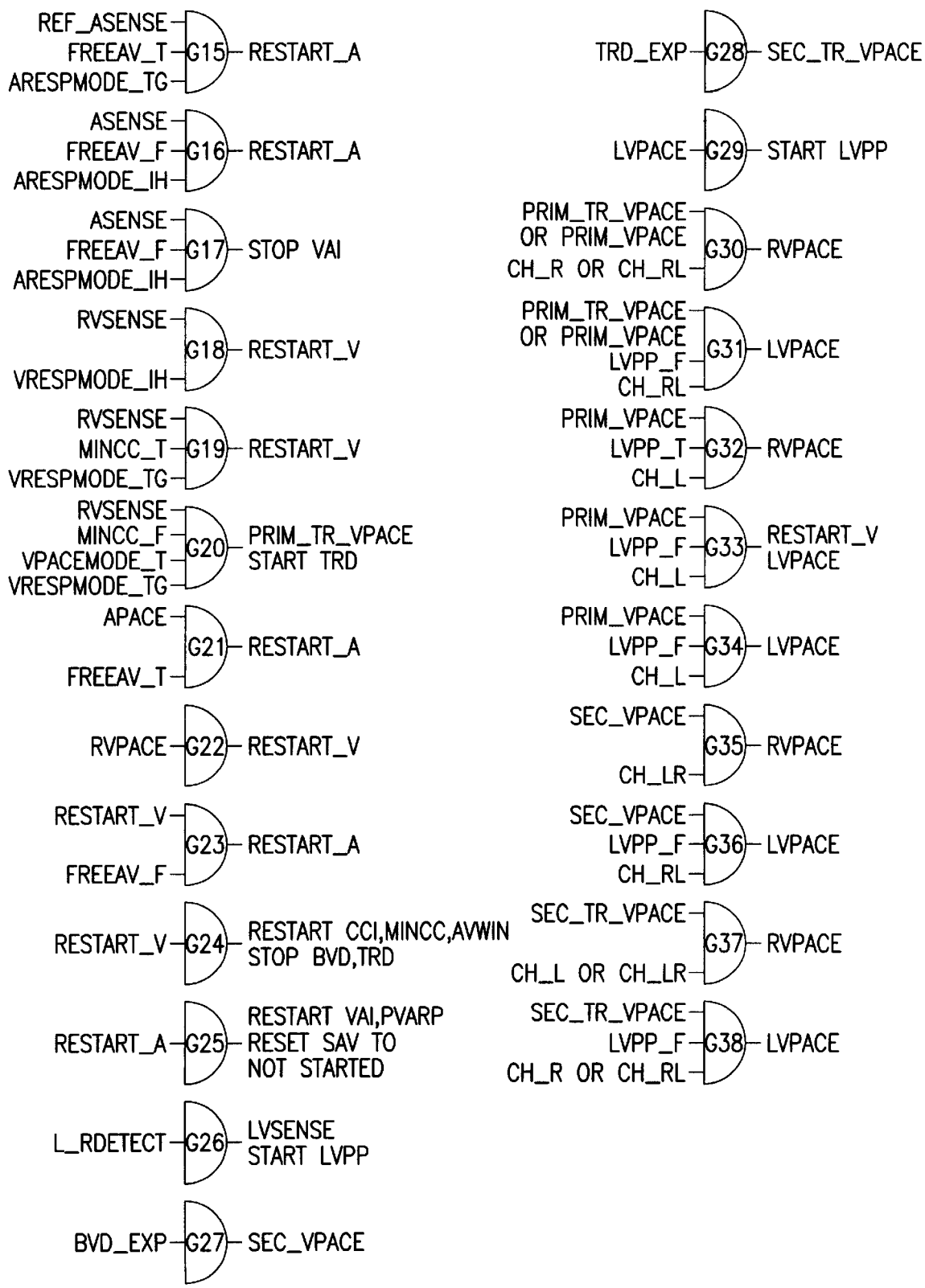

FIGS. 3A and 3B show the logic of the combinational logic array 100 in the form of status signals signifying the occurrence of different events and conditions ANDed together through gates G1 through G38 to produce various actions. A primary ventricular pace command (PRIM_VPACE) is produced by gate G1 if the CCI interval timer is expired (CCI_EXP) and the device is in a ventricular paced mode (VPACEMODE_T). The biventricular delay timer BVD is also started, and the sensed AV interval timer SAV is stopped. If the device is not in a ventricular paced mode (VPACEMODE_F), expiration of the CCI timer causes assertion of RESTART_V by gate G2 which restarts the ventricular timers as explained below. Gate G6 produces a primary ventricular pace command PRIM_VPACE, starts the BVD timer, and stops the CCI timer upon expiration of the sensed AV interval (SAV_EXP) if the minimum cardiac cycle timer is expired or stopped (MINCC_F) and the device is in a ventricular pacing mode (VPACEMODE_T). Gate G7 produces a primary ventricular pace command PRIM_VPACE and starts the BVD timer if the MINCC timer is expired (MINCC_EXP), the sensed AV interval timer is expired or stopped (SAV_F), and the device is in a ventricular pacing mode. Expiration of the BVD timer (BVD_EXP) causes assertion of the secondary ventricular pace command SEC_VPACE by gate G27. The secondary triggered ventricular pace command SEC_TR_VPACE is asserted by gate G28 upon expiration of the triggered delay timer TRD (TRD_EXP).

Gates G3 through G5 define the actions taken upon expiration of the ventriculoatrial interval timer VAI (VAI_

EXP). If the device is not in an atrial pacing mode (APACEMODE_F) and the FREEAV bit is set (FREEAV_T), RESTART_A is asserted. If the device is in an atrial pacing mode (APACEMODE_T) and the atrial protection period timer is not running (APP_N), expiration of VAI causes an atrial pace command APACE. No action is taken upon expiration of VAI if the device is not in an atrial pacing mode and the FREEAV bit is not set.

Gate G8 generates an atrial pace command APACE if the atrial protective period timer is expired (APP_EXP), the VAI timer is expired or stopped (VAI_F), the AVWIN timer is running (AVWIN_T), and the device is in an atrial pacing mode (APACEMODE_T). The PDETECT signal indicates detection of a P wave (i.e., atrial depolarization) by the sensing channel. If a P wave is detected while the post-ventricular refractory period timer is running (PVARP_T), the atrial protective period timer APP is started and REF_ASENSE (indicating an atrial sense during PVARP) is asserted by gate G9. If the atrial protective period timer APP is already running when a P wave is detected during PVARP, APP is restarted by gate G10. If a P wave is detected while the VAI timer is running (VAI_LT), the post-ventricular atrial refractory period timer is expired or stopped, and the atrial protective period timer is expired or not started (APP_N), gate G11 generates an atrial sense (ASENSE).

Gate 12 indicates that detection of a right ventricular R wave (i.e., detection of right ventricular depolarization) unconditionally generates a right ventricular sense (RVVSENSE). Gate 26 unconditionally generates a left ventricular sense LVSENSE and starts the left ventricular protection period timer LVPP upon assertion of a left ventricular detect signal L_RDETECT. The LVPP timer is also started upon generation of a left ventricular pace LVPACE by gate G29.

If an atrial sense is generated while the sensed AV interval timer SAV is idle (SAV_I) and the device is in an atrial tracking mode (ARESPMODE_TK), gate G13 starts the SAV timer and stops the VAI timer. If an atrial sense is generated while the device is in an atrial pacing mode and an atrial triggered mode (ARESPMODE_TG), gate G14 generates an atrial pace command and stops the VAI timer. timers are divided into atrial and ventricular timers. If the FREEAV bit is set, the atrial and ventricular timers are restarted independently by assertion of the signals RESTART_A and RESTART_V, respectively. If the FREEAV bit is not set, RESTART_V restarts both the atrial and ventricular timers. Gate G24 indicates that if RESTART_V is asserted, the ventricular timers CCI, MINCC, and AVWIN are restarted. If the FREEAV bit is not set, RESTART_V causes the assertion of RESTART_A through gate G23. Gate G25 defines RESTART_A as restarting the atrial timers VAI and PVARP, and resetting SAV to not started.

RESTART_A is asserted by gate G15 if REF_ASENSE is asserted, the FREEAV bit is set, and the device is operating in an atrial triggered mode (ARESPMODE_TG). RESTART_A is asserted by gate G16 if an atrial sense is generated, the FREEAV bit is set, and the device is operating in an atrial inhibited mode. The VAI timer is stopped by gate G17 if an atrial sense is generated, the FREEAV bit is not set, and the device is operating in an atrial inhibited mode. RESTART_A is asserted by gate G21 if an atrial pace command is generated and the FREEAV bit is set.

RESTART_V is asserted by gate G18 if a right ventricular sense is generated while the device is operating in a ventricular inhibited pacing mode. RESTART_V is asserted by gate G19 if a right ventricular sense is generated, the device is operating in a ventricular triggered mode, and the minimum cardiac cycle timer is running. RESTART_V is unconditionally asserted by gate G22 if a right ventricular pace command RVPACE is generated. A primary triggered ventricular pace command PRIM_TR_VPACE is generated and the TRD timer is started by gate G20 if a right ventricular sense RVSENSE is generated, the MINCC timer is stopped or expired, and the device is operating in a ventricular pacing and ventricular triggered mode.

Gates G30 through G38 generate either right or left ventricular paces in accordance with the assertion of signals described earlier and the control bits of register CR1. A right ventricular pace RVPACE is generated by gate G30 upon assertion of either PRIM_TR_PACE or PRIM_VPACE and if right or right-left ventricular pacing is enabled (CH_R or CH_RL). RVPACE is also generated as a backup in left ventricular pacing by gate G32 if PRIM_VPACE is asserted, the LVPP timer is unexpired, and the device is in a left ventricular pacing mode(CH_L). RVPACE is generated as a secondary pace by gate G35 if the device is in left-right biventricular pacing mode upon assertion of SEC_VPACE. RVPACE is generated as a secondary triggered pace by gate G37 upon assertion of SEC_TR_VPACE if the device is in left or left-right biventricular pacing mode (CH_R or CH_LR).

A left ventricular pace LVPACE is generated by gate G31 upon assertion of either PRIM_TR_PACE or PRIM_VPACE, if right-left biventricular pacing is enabled (CH_RL), and the LVPP timer has expired (LVPP_F). Gate G34 asserts LVPACE upon assertion of PRIM_VPACE if the device is in left-only ventricular pacing mode (CH_L) and the LVPP timer is unexpired. Gate G36 generates LVPACE as a secondary pace if SEC_VPACE is asserted, the LVPP timer is unexpired, and right-left biventricular pacing is enabled (CH_RL). Gate G38 generates LVPACE as a secondary triggered pace upon assertion of SEC_IR_PACE if the LVPP timer is unexpired and right or right-left ventricular pacing is enabled.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac pacemaker, comprising:
  an interval timer;
  a compare register for storing at least one specified limit value;
  a comparator for generating a specific timer expiration signal when an output of the timer equals a specific limit value;
  at least one sensing/pacing channel, each such channel comprising an electrode for disposing near a chamber of the heart, a stimulus generator for outputting pacing pulses, and a sense amplifier for detecting depolarization signals;
  a combinational logic array for generating sense signals from the detected depolarization signals, triggering the stimulus generator upon generation of a timer expiration signal by the comparator, and resetting the interval timer upon generation of a sense or pace; and,
  a microprocessor-based controller for updating the compare register in accordance with instructions programmed therein.

2. The pacemaker of claim 1 further comprising:

a control register for containing a mode value stored by the microprocessor-based controller; and, wherein the combinational logic array enables or disables timers and triggering of paces by timer expirations and/or sense signals so as to cause the pacemaker to operate in a particular pacing mode in accordance with the mode value stored in the control register.

3. A cardiac pacemaker, comprising:

a cardiac cycle interval (CCI) timer, resetting of which defines a cardiac cycle;

a CCI compare register for storing a specified CCI limit value;

a CCI comparator for generating a timer expiration signal when an output of the timer equals the CCI limit value;

a first ventricular sensing/pacing channel comprising an electrode for disposing near a ventricle of the heart, a stimulus generator for outputting pacing pulses, and a sense amplifier for detecting ventricular depolarization signals;

a combinational logic array for generating sense signals from the detected depolarization signals, for triggering the stimulus generator to generate a pacing pulse upon expiration of the CCI timer, and for resetting the CCI timer upon generation of a ventricular sense signal or pacing pulse; and, a microprocessor-based controller for updating the compare register between cardiac cycles in accordance with instructions programmed therein.

4. The pacemaker of claim 3 further comprising:

an atrial sensing channel comprising an electrode for disposing near an atrium of the heart and a sense amplifier for detecting atrial depolarization signals;

a sensed atrio-ventricular interval (SAV) timer;

a SAV compare register for storing a specified SAV limit value as updated by the microprocessor-based controller;

a SAV comparator for generating a timer expiration signal when an output of the SAV timer equals the SAV limit value; and, wherein the combinational logic array triggers the ventricular stimulus generator upon expiration of the SAV timer, stops the SAV timer upon a ventricular sense or pace, and resets the SAV timer upon an atrial sense.

5. The pacemaker of claim 4 further comprising:

an atrial stimulus generator for outputting a voltage pulse to an electrode disposed near the atrium;

a ventriculo-atrial interval (VAI) timer;

a VAI compare register for storing a specified VAI limit value as updated by the microprocessor-based controller;

a VAI comparator for generating a timer expiration signal when an output of the VAI timer equals the VAI limit value; and, wherein the combinational logic array triggers the atrial stimulus generator upon expiration of the VAI timer, stops the VAI upon an atrial sense or pace, and resets the VAI timer upon a ventricular sense or pace.

6. The pacemaker of claim 5 further comprising:

a control register for containing a mode value stored by the microprocessor-based controller; and, wherein the combinational logic array enables or disables timers and triggering of paces by timer expirations and/or sense signals so as to cause the pacemaker to operate in a particular pacing mode in accordance with the mode value stored in the control register.

7. The pacemaker of claim 6 further comprising:

a minimum cardiac cycle (MINCC) timer;

a MINCC compare register for storing a specified MINCC limit value as updated by the microprocessor-based controller;

a MINCC comparator for generating a timer expiration signal when an output of the MINCC timer equals the MINCC limit value; and, wherein the combinational logic array, when the pacemaker is programmed to operate in an atrial tracking mode, prevents delivering a ventricular pace upon expiration of the SAV timer if the MINCC timer is unexpired.

8. The pacemaker of claim 7 further comprising:

a post-ventricular refractory period (PVARP) timer;

a PVARP compare register for storing a specified PVARP limit value as updated by the microprocessor-based controller;

a PVARP comparator for generating a timer expiration signal when an output of the PVARP timer equals the PVARP limit value; and, wherein the combinational logic array resets the PVARP timer upon generation of a ventricular sense signal and prevents generation of an atrial sense signal if the PVARP timer is unexpired.

9. The pacemaker of claim 8 further comprising:

an atrial protective period (APP) timer;

an APP compare register for storing a specified APP limit value as updated by the microprocessor-based controller;

an APP comparator for generating a timer expiration signal when an output of the APP timer equals the APP limit value; and, wherein the combinational logic array starts the APP timer upon an atrial sense and prevents generation of an atrial sense or an atrial pace if the APP timer is unexpired.

10. The pacemaker of claim 9 further comprising:

a minimum AV window (AVWIN) timer;

a AVWIN compare register for storing a specified AVWIN limit value as updated by the microprocessor-based controller, a AVWIN comparator for generating a timer expiration signal when an output of the AVWIN timer equals the AVWIN limit value; and, wherein the combinational logic array starts the AVWIN timer after a ventricular sense or pace and prevents generation of an atrial pace after expiration of the APP timer if the AVWIN timer is expired.

11. The pacemaker of claim 8 wherein the control register further comprises a free atrio-ventricular interval (FAV) control bit such that when the bit is set, the combinational logic array resets the VAI and PVARP timers after an atrial pace, or an atrial sense if the pacemaker is operating in an atrial inhibited pacing mode, instead of after a ventricular sense or pace.

12. The pacemaker of claim 8 wherein the control register further comprises a noise inhibit NISI) control bit such that when the bit is set, the combinational logic array inhibits generation of pacing pulses if a noise level as sensed by the sensing channels exceeds a specified level.

13. The pacemaker of claim 6 further comprising:
a second ventricular sensing/pacing channel, the channel comprising an electrode for disposing near a ventricle of the heart, a stimulus generator for outputting pacing pulses, and a sense amplifier for detecting ventricular depolarization signals; and,
wherein a particular biventricular pacing mode is specified by a portion of the mode value stored in the control register.

14. The pacemaker of claim 13 further comprising:
a biventricular delay (BVD) timer,
a BVD compare register for storing a specified BVD limit value as updated by the microprocessor-based controller;
a BVD comparator for generating a timer expiration signal when an output of the BVD timer equals the BVD limit value; and,
wherein the combinational logic array starts the BVD timer after a first ventricular sense or pace and causes generation of a second ventricular pace through the second ventricular pacing channel upon expiration of the BVD timer if the pacemaker is in a biventricular pacing mode as specified by the mode value of the control register.

15. The pacemaker of claim 13 further comprising:
a triggered delay (TRD) timer;
a TRD compare register for storing a specified TRD limit value as updated by the microprocessor-based controller;
a TRD comparator for generating a timer expiration signal when an output of the TRD timer equals the TRD limit value; and,
wherein the combinational logic array starts the TRD timer after a first ventricular pace is triggered by a ventricular sense and causes generation of a second ventricular pace through the second ventricular pacing channel upon expiration of the TRD timer if the pacemaker is in a biventricular triggered pacing mode as specified by the mode value of the control register.

16. The pacemaker of claim 13 further comprising:
an left ventricular protective period (LVPP) timer;
an LVPP compare register for storing a specified LVPP limit value as updated by the microprocessor-based controller;
an LVPP comparator for generating a timer expiration signal when an output of the LVPP timer equals the LVPP limit value; and,
wherein the combinational logic array starts the LVPP timer upon generation of a left ventricular sense or pace and prevents generation of a left ventricular pace if the LVPP timer is unexpired.

17. The pacemaker of claim 8 wherein the combinational logic array generates interrupts to the microprocessor-based controller upon expiration of a timer, generation of a sense signal, or generation of a pacing output.

18. The pacemaker of claim 8 wherein the combinational logic array allows inputs from the microprocessor-based controller to command generation of a pace output.

19. The pacemaker of claim 8 wherein the combinational logic array allows inputs from the microprocessor-based controller to command resetting of a timer.

20. The pacemaker of claim 8 wherein the combinational logic array allows inputs from the microprocessor-based controller to command the timers to be reset in accordance with the programmed mode as if a pace were output.

21. The pacemaker of claim 8 further comprising an event buffer register readable by the microprocessor-based controller, wherein the combinational logic array stores event values in the event buffer register corresponding to occurrence of specified events, including generation of sense signals, generation of pacing outputs, and expiration of timers.

22. The pacemaker of claim 17 wherein the combinational logic array stores a time stamp along with each stored event value.

23. The pacemaker of claim 17 wherein the combinational logic array stores interval data as part of certain stored event values.

24. The pacemaker of claim 17 wherein the control register further comprises a noise inhibit (NSI) control bit such that when the bit is set, the combinational logic array inhibits generation of pacing outputs if a noise level as sensed by the sensing channels exceeds a specified level, and further wherein the combinational logic array stores event values corresponding to inhibited pacing outputs.

* * * * *